United States Patent [19]

Itoi

[11] Patent Number: 6,006,584
[45] Date of Patent: Dec. 28, 1999

[54] GAS CHROMATOGRAPH MASS SPECTROMETER

[75] Inventor: Hiroto Itoi, Kyoto, Japan

[73] Assignee: Shimadzu Corporation, Kyoto, Japan

[21] Appl. No.: 09/048,313

[22] Filed: Mar. 26, 1998

[30] Foreign Application Priority Data

Mar. 31, 1997 [JP] Japan .......................... H9-097997 (P)

[51] Int. Cl.$^6$ ............................. H01J 49/04; G01N 30/72
[52] U.S. Cl. ......................... 73/23.37; 73/23.42; 250/288
[58] Field of Search ................................ 73/23.37, 23.4, 73/23.42, 23.35, 61.61; 96/106; 250/282, 281, 288, 284

[56] References Cited

U.S. PATENT DOCUMENTS 4,794,252 12/1988 Bateman et al. ......................... 250/288
4,942,296 7/1990 Jones ........................................ 250/288

Primary Examiner—Michael Brock
Attorney, Agent, or Firm—Armstrong, Westerman, Hattori, McLeland and Naughton

[57] ABSTRACT

A GC/MS includes a sample conduit 22 between a gas chromatographic column and an ionizing chamber 31 which is placed in a vacuum housing 35, and the heating mechanism for the sample conduit 22 and the ionizing chamber 31 includes: a heating unit 23 provided in contact with the sample conduit 22 for heating the sample conduit 22; a connecting bar 25 provided between the heating unit 23 and the ionizing chamber 31 for conducting heat from the heating unit 23 to the ionizing chamber 31 with a first thermal resistance; and a depressed cap 26 provided between the ionizing chamber 31 and the vacuum housing 35 for conducting heat from the ionizing chamber 31 to the vacuum housing 35 with a second thermal resistance. Since the sample conduit 22 is heated directly by the heating unit 23, the temperature of the sample conduit 22 is almost the same as that of the heating unit 23. Since the vacuum housing 35 has a large heat capacity and it is normally at room temperature, heat is conducted from the heating unit 23 to the ionizing chamber 31 via the connecting bar 25, and heat is conducted from the ionizing chamber 31 to the vacuum housing 35 via the depressed cap 26. At equilibrium, the temperature of the ionizing chamber 31 is at a value between those of the heating unit 23 and the vacuum housing 35, and the value can be determined by appropriately setting the ratio of the first and second thermal resistances of the thermal conducting members 25 and 26.

6 Claims, 3 Drawing Sheets

GAS CHROMATOGRAPH MASS SPECTROMETER

The present invention relates to a gas chromatograph mass spectrometer (GC/MS) with an interface section between the gas chromatograph (GC) section and the mass spectrometer (MS) section.

BACKGROUND OF THE INVENTION

In a GC/MS, a sample is separated into a series of components of a column in the GC section, and the components are introduced through the interface section into the MS section, where the components are sequentially mass analyzed. As shown in FIG. 3, carrier gas flows at a constant rate through the gas chromatographic column 12 which is heated by the column oven 13 at an appropriate temperature in the GC section 10. When a sample is injected into the injector 11, the sample is vaporized and carried by the carrier gas to the column 12. While the sample passes through the column 12, the sample is separated into its constituent components with respect to the passing time, whereby the components are sequentially introduced through the interface section 20 into the ionizing chamber 31 of the MS section 30. The molecules of the components are ionized by electrons (in the case of electron impact ionization) in the ionizing chamber 31, and the ions are converged by the ion lens 32 and introduced into the quadrupole filter 33 (or other mass spectrometer). On the four rods of the quadrupole filter 33 is applied a combined voltage of a DC (direct current) voltage and an RF (radio frequency) voltage, and such ions having a certain mass number (i.e., the ratio of mass to electrical charge m/z of the ion) corresponding to the applied voltage can pass the quadrupole filter 33 and enter the ion detector 34.

The column 12 is set at a temperature in the range of 100–300° C., where the temperature depends on the component to be analyzed or on other factors. In many cases, the temperature is set according to the boiling point of the component. If the temperature of the sample decreases at the end of the column 12, the flow of the sample decreases and the accuracy of the analysis deteriorates. That is why the interface section 20 is heated at about the same temperature as that of the column 12. The ionizing chamber 31 is heated at a temperature appropriate for the stable ionization of the molecules, which is normally tens of degree centigrade lower than that of the interface section 20.

The interface section 20 and the ionizing chamber 31 are thus heated separately, in conventional GC/MSs, and a heating unit is respectively provided and attached to each of the interface section 20 and the ionizing chamber 31. A primary disadvantage of the conventional configuration is that it raises the cost of the GC/MS. Another disadvantage is that the maintenance of the ionizing chamber 31 (e.g., cleaning) is troublesome since the ionizing chamber 31 is contained in a vacuum housing 35 made of stainless steel. First the lead wires are detached from the housing 35; the ionizing chamber 31 is drawn out of the housing 35; and then the heating unit is detached from the ionizing chamber 31.

FIG. 4 shows an improved interface section 20, in which a capillary tube 21 connected to the gas chromatographic column (not shown in FIG. 4) is inserted into and held by the interface line 22 made of stainless steel, and a heating unit 23 is attached to the interface line 22. At the end of the interface line 22 toward the MS section 30 is attached a connecting ring 24 having an appropriate thermal resistance. The connecting ring 24 thermally connects the interface line 22 and the ionizing chamber 31. Since, as described before, the temperature of the ionizing chamber 31 can be lower than that of the interface line 22, the interface line 22 is directly heated by the heating unit 23, and the ionizing chamber 31 is heated by the heat from the interface line 22 conducted through the connecting ring 24. This configuration requires only a single heating unit 23 and no heating unit is needed in the ionizing chamber 31, which reduces the cost and facilitates the maintenance of the ionizing chamber 31.

The GC/MS shown in FIG. 4 still has some drawbacks. Since the ionizing chamber 31 is heated by the heat from the interface line 22, the temperature of the ionizing chamber 31 is not stabilized until the temperature of the interface line 22 is stabilized. This requires a prolonged period of time before a proper sample analysis can be started. Another drawback is that the long interface line 22 inevitably invites non-uniformity in the temperature since a part of the interface line 22 is directly heated by the heating unit 23 while the other part is not heated but is deprived of the heat by the connecting ring 24. This deteriorates the accuracy of the analysis. Still another drawback is that precise temperature control of the ionizing chamber 31 is difficult because it is heated indirectly via the connecting ring 24.

SUMMARY OF THE INVENTION

The present invention addresses such problems, and provides a GC/MS having a simpler structure and a better heating mechanism for the interface section and the ionizing chamber.

According to the invention, a GC/MS includes a sample conduit between a gas chromatographic column and an ionizing chamber which is placed in a vacuum housing, and the GC/MS further includes:

a heating unit provided in contact with the sample conduit for heating the sample conduit;

first thermal conducting means provided between the heating unit and the ionizing chamber for conducting heat from the heating unit to the ionizing chamber with a first thermal resistance; and second thermal conducting means provided between the ionizing chamber and the vacuum housing for conducting heat from the ionizing chamber to the vacuum housing with a second thermal resistance.

Third thermal conducting means may be provided between the sample conduit and the vacuum housing. The third thermal conducting means should have a larger thermal resistance than those of the first and second thermal conducting means.

The sample conduit (or the interface line) and the ionizing chamber are thermally separated in the present invention, and they are heated independently by the heating unit: the sample conduit is heated directly by the heating unit and the ionizing chamber is heated indirectly via the first thermal conducting means. The temperature of the sample conduit is therefore almost the same as that of the heating unit. The vacuum housing has a large heat capacity since it houses the ionizing chamber, and its temperature is very low (normally, room temperature) compared to that of the heating unit. Thus heat is conducted from the heating unit to the ionizing chamber via the first thermal conducting means, and heat is conducted from the ionizing chamber to the vacuum housing via the second thermal conducting means. At equilibrium, the temperature of the ionizing chamber is at a value between those of the heating unit and the vacuum housing, and the value is determined by the ratio of the first and second thermal resistances of the first and second thermal conducting means. The first and second thermal resistances of the first and second thermal conducting means can be set by using metals of appropriate thermal conductivities, and also by adjusting the cross sectional area of the members with respect to the flow of heat. Each of the thermal conducting means can be constituted by a plurality of members, in which case the thermal resistance can be easily adjusted by combining those of the constituent members.

The third thermal conducting means having a large thermal resistance thermally insulates the sample conduit which is heated by the heating unit from the vacuum housing which has a very large heat capacity and is normally at room temperature. This assures the rapid heating and precise temperature control of the thermal conduit and also those of the ionizing chamber.

Since, as described above, the sample conduit and the ionizing chamber are independently heated by the heating unit, they are almost unaffected by each other when heated. Owing to this fact, the temperatures of the sample conduit and the ionizing chamber can be respectively controlled with precision and can be stabilized in a shorter period of time.

The sample conduit gives heat only to the sample flowing in it and to the ambient air, so that the temperature difference between the part near the heating unit and the part at a distance from it is smaller compared to the conventional GC/MS described before.

It is easier to set the temperatures of the sample conduit and the ionizing chamber at appropriate values in the present invention. The reason is as follows. The temperature of the sample conduit is almost the same as that of the heating unit, and the temperature of the ionizing chamber is determined by the ratio of the thermal resistances of the first and second thermal conducting means.

There is no need to provide a separate heating unit to the ionizing chamber. This reduces the cost of the GC/MS according to the present invention, and eliminates the troublesome maintenance of the ionizing chamber described above.

DETAILED DESCRIPTION OF A PREFERRED EMBODIMENT

Figure 1:
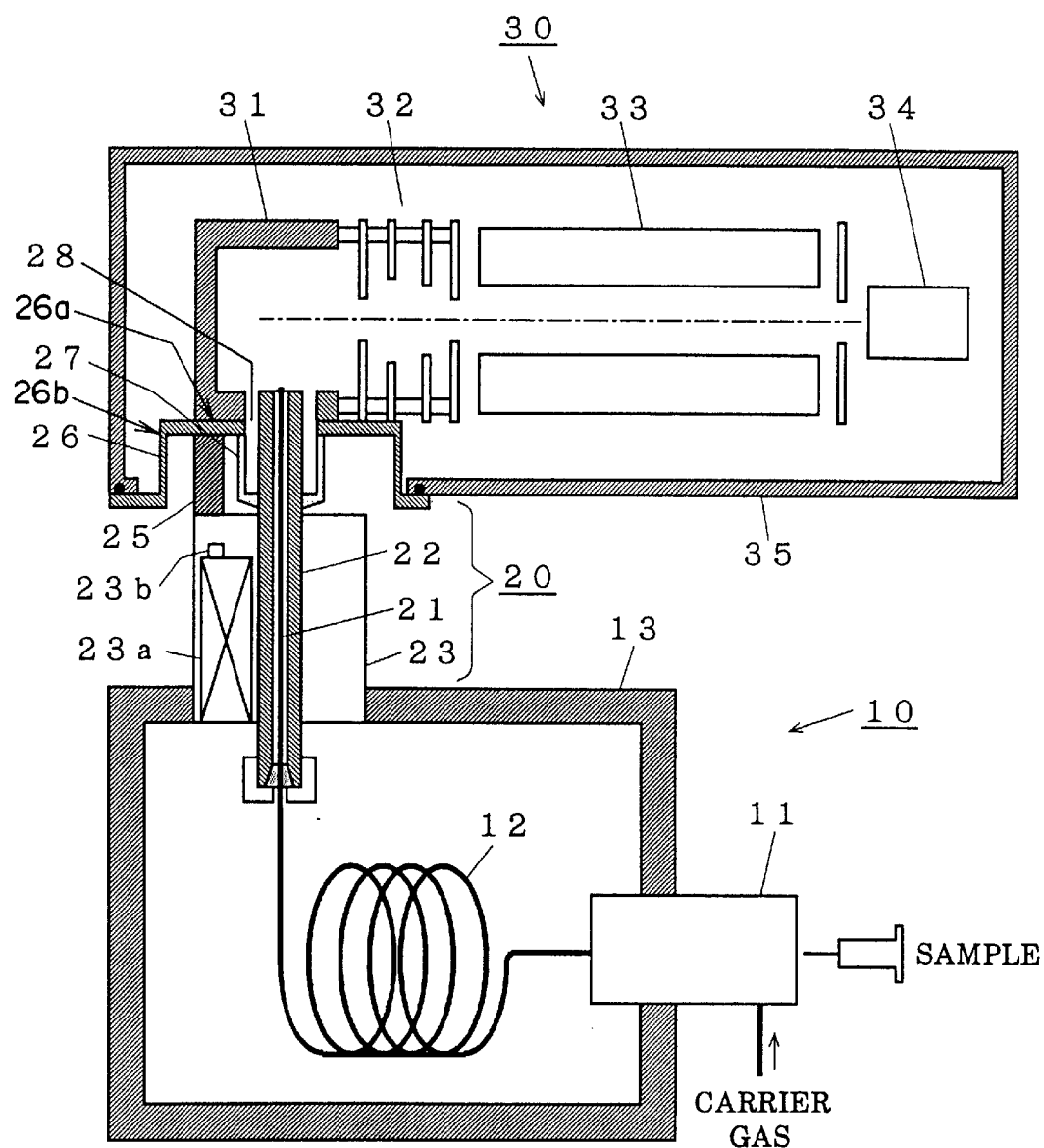
FIG. 1 is a cross sectional view of a GC/MS embodying the present invention.
Figure 4:
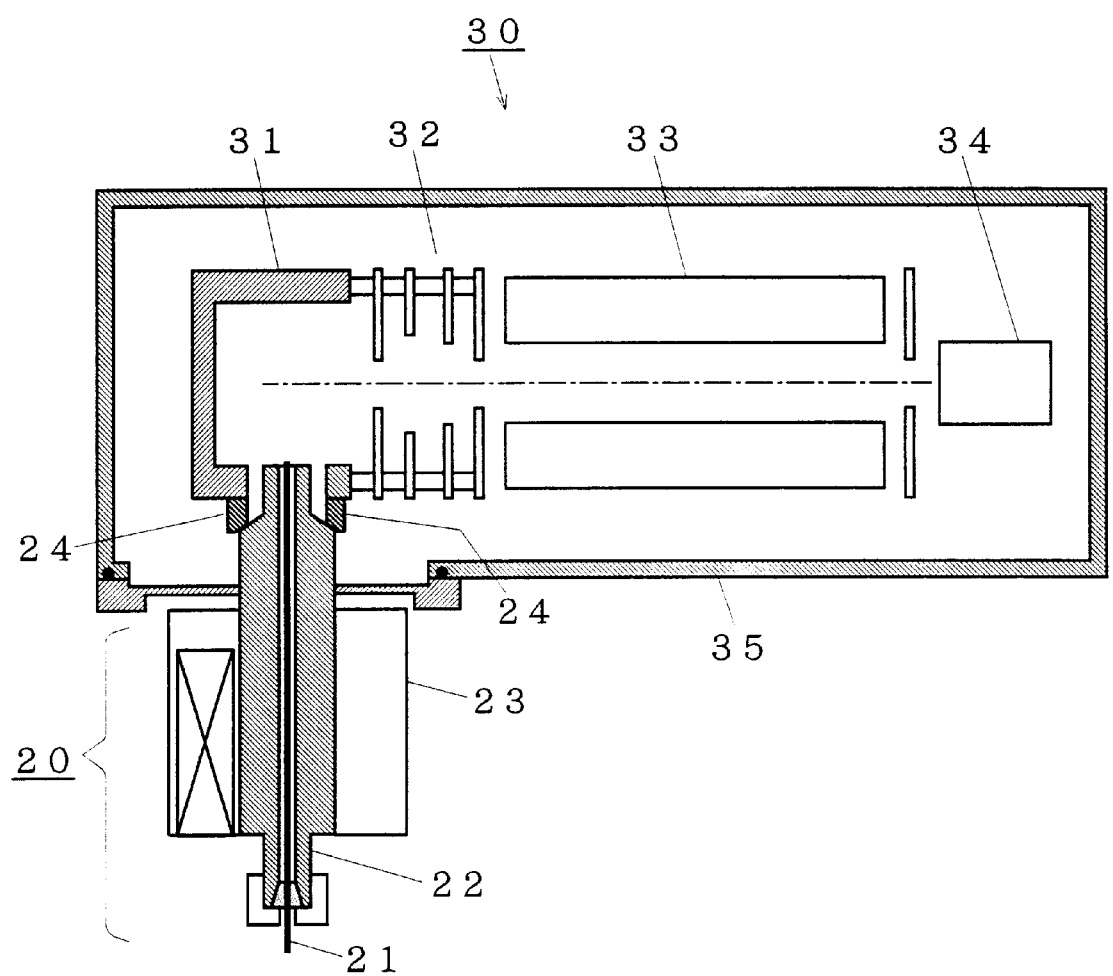
FIG. 4 is cross sectional view around the interface section of a conventional GC/MS.

A gas chromatograph mass spectrometer (GC/MS) embodying the present invention is described. FIG. 1 shows a cross sectional view of the GC/MS where the mass spectrometer (MS) section 30 is similar to that described before with reference to FIG. 4. The interface section 20 is characteristic in the present embodiment where a heating unit 23 is attached around the interface line 22. The heating unit 23 includes a heating cartridge 23a and a temperature sensor 23b, and the power to the heating cartridge 23a is adjusted so that the temperature detected by the sensor 23b is maintained at a preset value.

The interface line 22 is directly heated by the heating unit 23 at the contacting face. A connecting bar 25 is attached to the heating unit 23, and the connecting bar 25 is connected to a side wall of the ionizing chamber 31 via a depressed cap 26. The depressed cap 26 is adapted to the opening of the vacuum housing 35 of the MS section 30, which is made of stainless steel, and contacts the ionizing chamber 31 in the vacuum housing 35. A hole 28 is formed in the depressed cap 26 for passing the interface line 22 through. A closing cap 27 connects the periphery of the hole 28 and that of the interface line 22, so that the ionizing chamber 31 is maintained airtight in the vacuum housing 35. The closing cap 27 may be made of similar material as the connecting bar 25 and the depressed cap 26, but it is designed to have a very large thermal resistance so that the ionizing chamber 31 and the interface line 22 are thermally insulated.

Figure 2:
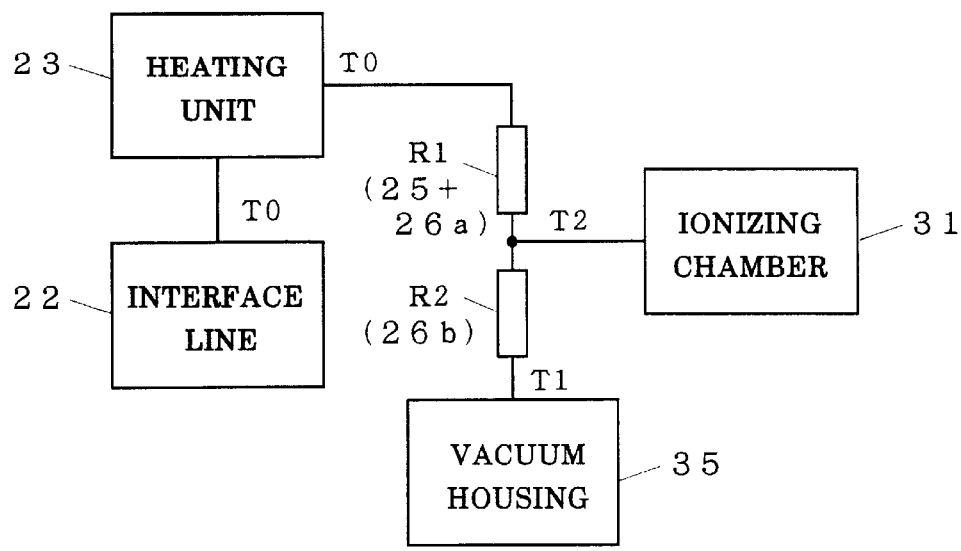
FIG. 2 is a thermal connection diagram of the embodiment.
Figure 3:
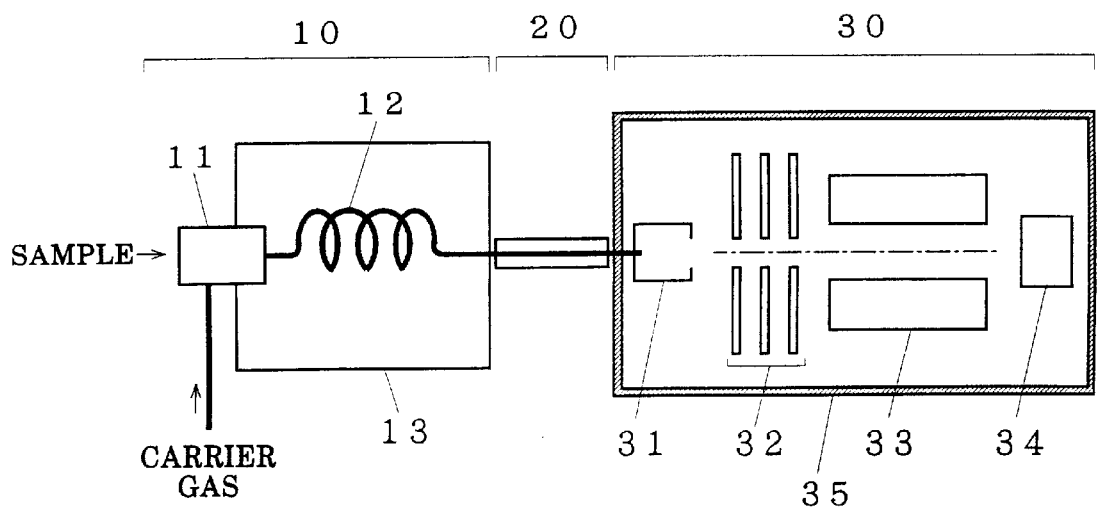
FIG. 3 is an overall view of an ordinary GC/MS.

The thermal connection diagram of the system is shown in FIG. 2. The heating unit 23 and the ionizing chamber 31 are connected by a first thermal conducting means which is constituted by the connecting bar 25 and a small part 26a of the depressed cap 26, and has a thermal resistance R1. The ionizing chamber 31 and the vacuum housing 35 are connected by a second thermal conducting means which is constituted by a part 26b of the depressed cap 26, and has a thermal resistance R2. The heating unit 23 is heated and maintained at a temperature T0. The temperature T0 is set according to the object component and is normally in the range 100–300° C. The interface line 22 is heated directly by the heating unit 23 and is thus maintained at the temperature T0. The vacuum housing 35, on the other hand, is in contact with the ambient air and the heat capacity is substantially large so that the temperature T1 of the vacuum housing 35 is maintained near the ambient (room) temperature. Thus by setting the ratio R1/R2 of the thermal resistances R1 and R2 described above at an appropriate value, the temperature T2 of the ionizing chamber 31 can be determined at a desired value between T0 and T1.

When the temperatures are stable and at an equilibrium, $$T2 = R2 \cdot (T0 - T1)/(R1 + R2) + T1$$

Since, as described above, the temperature of the heating unit 23 is precisely controlled and the vacuum housing 35 has a very large heat capacity, the temperatures T0 and T1 are almost stable. The temperature T2 of the ionizing chamber 31 thus comes to equilibrium rapidly after heating is begun, and the equilibrium temperature is maintained at a stable level.

Various kinds of material can be used for the connecting bar 25, the depressed cap 26 and for the closing cap 27. When smaller thermal resistance is required, highly conductive metals such as aluminum, copper or brass are used. When larger thermal resistances are required, less conductive metals such as stainless steel are suited. It is also possible to adjust the thermal resistance (or conduction of heat) by changing the cross sectional area of the members. For the closing cap 27 that requires a very large thermal resistance, therefore, stainless steel is used and the cross sectional area is set as small as possible so long as adequate structural strength is assured.

Obviously, many modifications and variations of the present invention are possible in light of the above teachings. It is therefore to be understood that within the scope of the appended claims, the invention may be practiced other than as specifically described.

What is claimed is:

1. A gas chromatograph mass spectrometer (GC/MS) including a sample conduit provided to connect a gas chromatographic column and an ionizing chamber placed in a vacuum housing, the GC/MS comprising heating means provided in contact with the sample conduit for heating the sample conduit;

first thermal conducting means provided between the heating means and the ionizing chamber for conducting heat from the heating means to the ionizing chamber with a first thermal resistance;

second thermal conducting means provided between the ionizing chamber and the vacuum housing for conducting heat from the ionizing chamber to the vacuum housing with a second thermal resistance; and closing means for closing an opening provided in a wall of the vacuum housing for inserting the sample conduit into the vacuum housing, said closing means including third thermal conducting means provided between the sample conduit and the vacuum housing, said third thermal conducting means having a thermal resistance which is (i) larger than the thermal resistance of the first thermal conducting means and (ii) larger than the thermal resistance of the second thermal conducting means.

2. The GC/MS according to claim 1, wherein at least one of the first thermal conducting means, the second thermal conducting means and the third conducting means is constituted by a plurality of thermal conducting members.

3. The GC/MS according to claim 1, wherein the values of the first thermal resistance and the second thermal resistance are determined so that a ratio of the values renders a desired temperature of the ionizing chamber between a temperature of the heating means and a temperature of the vacuum housing.

4. The GC/MS according to claim 1, wherein each of the first thermal resistance and the second thermal resistance is set at a desired value by selecting a metal having an appropriate specific thermal resistance and by making a cross sectional area of the first thermal conducting means or the second thermal conducting means of an appropriate value.

5. A gas chromatograph mass spectrometer (GC/MS) including a sample conduit provided to connect a gas chromatographic column and an ionizing chamber placed in a vacuum housing, the GC/MS comprising heating means provided in contact with the sample conduit for heating the sample conduit;

first thermal conducting means provided between the heating means and the ionizing chamber for conducting heat from the heating means to the ionizing chamber with a first thermal resistance;

second thermal conducting means provided between the ionizing chamber and the vacuum housing for conducting heat from the ionizing chamber to the vacuum housing with a second thermal resistance; and third thermal conducting means provided between the sample conduit and the vacuum housing, the third thermal conducting means having a larger thermal resistance than those of the first and second thermal conducting means, wherein at least one of the first thermal conducting means and second thermal conducting means are constituted by a plurality of thermal conducting members, and the first thermal conducting means is constituted by a connecting bar for connecting the heating means and a part of a depressed cap for closing an opening of the vacuum housing and for connecting the connecting bar and the ionizing chamber.

6. The GC/MS according to claim 5, wherein the second thermal conducting means is constituted by another part of the depressed cap.

* * * * *